(12) United States Patent
Kim

(10) Patent No.: US 6,582,959 B2
(45) Date of Patent: *Jun. 24, 2003

(54) ANTIBODIES TO VASCULAR ENDOTHELIAL CELL GROWTH FACTOR

(75) Inventor: Kyung Jin Kim, San Francisco, CA (US)

(73) Assignee: Genentech, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/950,863

(22) Filed: Oct. 15, 1997

(65) Prior Publication Data

US 2002/0122797 A1 Sep. 5, 2002

Related U.S. Application Data

(63) Continuation of application No. 08/711,314, filed on Sep. 3, 1996, now abandoned, which is a continuation of application No. 08/558,042, filed on Nov. 13, 1995, now abandoned, which is a continuation of application No. 08/416,543, filed on Mar. 29, 1995, now abandoned, which is a continuation of application No. 08/185,291, filed on Jan. 24, 1994, now abandoned, which is a continuation of application No. 08/071,214, filed on Jun. 2, 1993, now abandoned, which is a continuation of application No. 07/677,215, filed on Mar. 29, 1991, now abandoned.

(51) Int. Cl.$^7$ .............................. C12N 5/12; C07K 16/22

(52) U.S. Cl. .................. 435/336; 435/326; 435/332; 435/346; 530/387.1; 530/388.1; 530/388.2; 530/388.24

(58) Field of Search ............... 424/133.1, 145.1, 424/130.1, 172.1; 530/387.3, 388.23, 387.1, 388.2, 388.7; 435/326, 336, 346

(56) References Cited

U.S. PATENT DOCUMENTS

| | | | |
|---|---|---|---|
| 4,456,550 A | | 6/1984 | Dvorak et al. |
| 4,816,567 A | * | 3/1989 | Cabilly et al. ............... 530/387 |
| 5,008,196 A | | 4/1991 | Connolly et al. |
| 5,036,003 A | | 7/1991 | Olander et al. |
| 5,219,739 A | * | 6/1993 | Tischler et al. |
| 5,725,856 A | * | 3/1998 | Hudziak et al. |

FOREIGN PATENT DOCUMENTS

| | | | |
|---|---|---|---|
| EP | 0 370 989 | 5/1990 | |
| EP | 370 989 | 5/1990 | ........... C12N/15/12 |
| WO | WO 90/13649 | 11/1990 | |
| WO | WO 91/02058 | 2/1991 | |
| WO | WO 92/14748 | 3/1992 | |

OTHER PUBLICATIONS

Leung, et al Science 246: 1306–1309 (1989).*
Voller, et al Diagnostic Horizons Z(1):1–6 (1978).*
Antibodies, a Laboratory Manual p. 72–77, 92–97, 128–135 & 141–157 1988 Cold Spring Harbor Press.*
Lerner Nature 299:592–596 1982.*
Waldmann Science 252:1657–1662 1991.*
Harris et al Tibtech 11:42–46 1993.*
Harlow and Lane, Anitbodies, a Laborotory Manual, Cold Spring Harbor Laborotory, New York, 1988; Antibody–Antigen Interactions, pp. 23–35.*
Connolly, et al., J. Biol. Chem. 264(33):20017–20024 (1989).
Ferrara & Henzel, Biochem. Biophys. Res. Commun. 161(2):851–858 (1989).
Keck, et al., Science 246:1309–1312 (1989).
Tischler, et al., Biochem. Biophys. Res. Commun. 165(3):1198–1206 (1989).
Connolly et al., "Human Vascular Permeability Factor" *Journal of Biological Chemistry* 264 (33):20017–20024 (Nov. 1989).
Ferrara et al., "Pituitary Follicular Cells Secrete a Novel Heparin–binding Growth Factor Specific for Vascular Endothelial Cells" *jBiochem. & Biophys. Res. Comm.* 161(2):851–858 (JUn. 15, 1989).
Folkman, J., "The Vascularization of Tumors" *Scientific American* 234(5) :59–73 (May 1976).
Harris et al., "Therapeutic Antibodies—The Coming of Age" *TIBTECH* 11:42–44 (Feb. 1993).
Keck et al., "Vascular Permeability Factor, An Endothelial Cell Mitogen Related PDGF" *Science* 246:1309–1312 (Dec. 1989).
Lerner, R.A., "Tapping the Immunological Repertoire to Produce Antibodies of Predetermined Specificity" *Nature* 299:592–596 (Oct. 1982).
Leung et al., "Vascular Endothelial Growth Factor is a Secreted Angiogenic Mitogen" *Science* 246:1306–1309 (Dec. 1989).

(List continued on next page.)

*Primary Examiner*—Phillip Gambel
(74) *Attorney, Agent, or Firm*—Steven X. Cui

(57) ABSTRACT

The present invention provides monoclonal antibodies, and portions thereof, which are capable of specifically binding to human vascular endothelial cell growth factor (hVEGF) or hVEGF-related protein. The invention also provides hybridoma cell lines that produce such monoclonal antibodies. The monoclonal antibodies of the invention are useful as therapeutic agents, either by themselves or in conjunction with cytotoxic or other chemotherapeutic agents, to treat diseases that are characterized by excessive vascular endothelial cell proliferation. The monoclonal antibodies of the invention also are useful in diagnostic and analytical methods for determining the presence of hVEGF or hVEGF related-protein in a test sample.

4 Claims, 3 Drawing Sheets

OTHER PUBLICATIONS

Oikawa et al., "A Novel Angiogenic Inhibitor Derived from Japanese Shark Cartilage (I). Extraction and Estimation of Inhibitory Activities Toward Tumor and Embryonic Angiogenesis" *Cancer Letters* 51:181–186 (1990).

Tischler et al., "Vascular Endothelial Growth Factor: A New Member of the Platelet–Derived Growth Factor Gene Family" *Biochem. & Biophys. Res. Comm.* 165(3):1198–1206 (1989).

Various authors *Antibodies, A Laboratory Manual*, ex:Cold Spring Harbor Press pp. 72–77, 92–87, 128–135, 141–157 (1988).

Voller et al., "The Enzyme Linked Immunosorbent Assay" *Diagnostic Horizons* 2 (1):1–6 (1978).

Waldman, Thomas A., "Monoclonal Antibodies in Diagnosis and Therapy" *Science* 252:1657–1662 (Jun. 21, 1991).

\* cited by examiner

ANTIBODIES TO VASCULAR ENDOTHELIAL CELL GROWTH FACTOR

This is a continuation of applications Ser. No. 08/711,314 filed on Sep. 3, 1996 now abandoned which is a continuation of Ser. No. 08/558,042 filed on Nov. 13, 1995, now abandoned, which is a continuation of application Ser. No. 08/416,543 filed on Mar. 29, 1995, now abandoned, which is a continuation of application Ser. No. 08/185,291 filed on Jan. 24, 1994, now abandoned, which is a continuation of application Ser. No. 08/071,214 filed on Jun. 2, 1993, now abandoned, which is a continuation of application Ser. No. 07/677,215 filed on Mar. 29, 1991, now abandoned, which applications are incorporated herein by reference and to which applications priority is claimed under 35 USC §120.

FIELD OF THE INVENTION

This application relates to hybrid cell lines (lymphocyte hybridomas) for the production of monoclonal antibodies to human vascular endothelial growth factor (hVEGF), to such homogeneous monospecific antibodies, and to the use of such antibodies for diagnostic and therapeutic purposes.

BACKGROUND OF THE INVENTION

The two major cellular components of the vasculature are the endothelial and smooth muscle cells. The endothelial cells form the lining of the inner surface of all blood vessels, and constitute a nonthrombogenic interface between blood and tissue. In addition, endothelial cells are an important component for the development of new capillaries and blood vessels. Thus, endothelial cells proliferate during the neovascularization associated with tumor growth and a variety of diseases, including psoriasis, arthritis, and diabetic retinopathy.

Various naturally occurring polypeptides reportedly induce the proliferation of endothelial cells. Among those polypeptides are the basic and acidic fibroblast growth factors (FGF), Burgess and Maciag, Annual Rev. Biochem., 58:575 (1989), platelet-derived endothelial cell growth factor (PD-ECGF), Ishikawa, et al., Nature, 338:557 (1989), and vascular endothelial growth factor (VEGF), Leung, et al., Science 246:1306 (1989); Ferrara & Henzel, Biochem. Biophys. Res. Commun. 161:851 (1989); Tischer, et al., Biochem. Biophys. Res. Commun. 165:1198 (1989); Ferrara, et al., PCT Pat. Pub. No. WO 90/13649 (published Nov. 15, 1990); Ferrara, et al., U.S. patent application Ser. No. 07/360,229.

VEGF was first identified in media conditioned by bovine pituitary follicular or folliculostellate cells. Biochemical analyses indicate that bovine VEGF is a dimeric protein with an apparent molecular mass of approximately 45,000 Daltons, and with an apparent mitogenic specificity for vascular endothelial cells. DNA encoding bovine VEGF was isolated by screening a cDNA library prepared from such cells, using oligonucleotides based on the amino-terminal amino acid sequence of the protein as hybridization probes.

Human VEGF was obtained by first screening a cDNA library prepared from human cells, using bovine VEGF cDNA as a hybridization probe. One cDNA identified thereby encodes a 165-amino acid protein having greater than 95% homology to bovine VEGF, which protein is referred to as human VEGF (hVEGF). The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung, et al., Science 246:1306 (1989).

Several additional cDNAs were identified in the human cDNA library that encode 121- and 189-amino acid hVEGF-related proteins. The 121-amino acid protein differs from hVEGF by virtue of the deletion of the 44 amino acids between residues 116 and 159 in hVEGF. The 189-amino acid protein differs from hVEGF by virtue of the insertion of 24 amino acids at residue 116 in hVEGF, and apparently is identical to human vascular permeability factor (hVPF). Keck, et al., Science 246:1309 (1989); Connolly, et al., J. Biol. Chem. 264:20017 (1989); Keck, et al., EPO Pat. Pub. No. 0 370 989 (published May 30, 1990).

In view of the fundamental role of vascular endothelial cell growth in many diseases, it is desirable to have a means of regulating the mitogenic effect of VEGF. It is also desirable to have a means of assaying for the presence of VEGF in normal and pathological conditions, and especially cancer.

SUMMARY OF THE INVENTION

The present invention is directed to monoclonal antibodies, and portions thereof, which are capable of specifically binding to hVEGF or hVEGF-related protein. The invention also is directed to hybridoma cell lines that produce such monoclonal antibodies. The monoclonal antibodies of the invention are useful as therapeutic agents, either by themselves or in conjunction with cytotoxic or other chemotherapeutic agents, to treat diseases that are characterized by excessive vascular endothelial cell proliferation. The monoclonal antibodies of the invention also are useful in diagnostic and analytical assays for determining the presence of hVEGF or hVEGF related-protein in a test sample.

DETAILED DESCRIPTION OF THE INVENTION

Figure 1A:
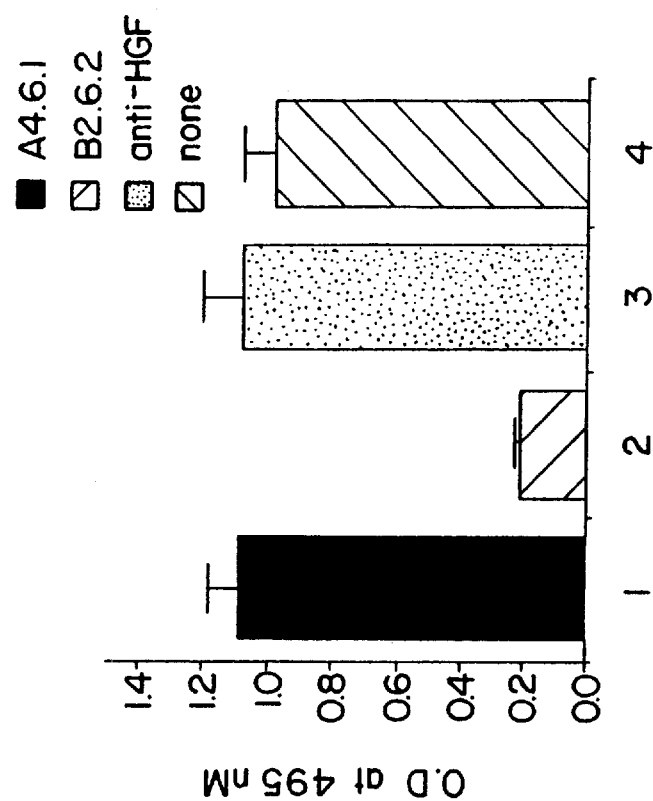
FIG. 1 shows the effect of anti-hVEGF monoclonal antibodies (A4.6.1 or B2.6.2) or an irrelevant anti-hepatocyte growth factor antibody (anti-HGF) on the binding of the anti-hVEGF monoclonal antibodies to hVEGF.

The present invention provides monoclonal antibodies, or portions thereof, which are capable of binding specifically to hVEGF or hVEGF-related protein. The term "hVEGF" refers to the 165-amino acid human vascular endothelial growth factor, and the term "hVEGF-related protein" refers to the 121- and 189-amino acid proteins, that are described by Leung, et al., Science 246:1306 (1989). The term "recombinant" used in reference to hVEGF or hVEGF-related protein refers to such proteins that are produced by recombinant DNA expression in a host cell.

The term "monoclonal antibody" as used herein refers to an antibody obtained from a population of substantially homogeneous antibodies, i.e., the individual antibodies comprising the population are identical except for possible naturally occurring mutations that may be present in minor amounts.

The monoclonal antibodies included within the scope of the invention include hybrid and recombinant antibodies (e.g. "humanized" antibodies) regardless of species of origin or immunoglobulin class or subclass designation, as well as antibody fragments (e.g., Fab, F(ab')$_2$, and Fv), so long as they are capable of binding specifically to hVEGF or hVEGF-related protein. Cabilly, et al., U.S. Pat. No. 4,816,567; Mage & Lamoyi, in *Monoclonal Antibody Production Techniques and Applications*, pp.79–97 (Marcel Dekker, Inc., New York, 1987).

Thus, the modifier "monoclonal" indicates the character of the antibody as being obtained from such a substantially homogeneous population of antibodies, and is not to be construed as requiring production of the antibody by any particular method. For example, the monoclonal antibodies of the invention may be made using the hybridoma method first described by Kohler & Milstein, Nature 256:495 (1975), or may be made by recombinant DNA methods. Cabilly, et al., U.S. Pat. No. 4,816,567.

In the hybridoma method, a mouse or other appropriate host animal is immunized with hVEGF or hVEGF-related protein by subcutaneous, intraperitoneal, or intramuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. Goding, *Monoclonal Antibodies: Principles and Practice*, pp.59–103 (Academic Press, 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies. Kozbor, J. Immunol. 133:3001 (1984). Brodeur, et al., *Monoclonal Antibody Production Techniques and Applications*, pp.51–63 (Marcel Dekker, Inc., New York, 1987).

Culture medium in which hybridoma cells are growing is assayed for production of monoclonal antibodies directed against hVEGF or hVEGF-related protein. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The monoclonal antibodies of the invention are those that preferentially immunoprecipitate hVEGF or hVEGF-related protein that is present in a test sample, or that preferentially bind to hVEGF or hVEGF-related protein in a binding assay.

In a preferred embodiment of the invention, the monoclonal antibody will have an affinity for binding hVEGF or hVEGF-related protein of at least about $10^9$ liters/mole, as determined, for example, by the Scatchard analysis of Munson & Pollard, Anal. Biochem. 107:220 (1980).

In another preferred embodiment of the invention, the monoclonal antibody is a neutralizing antibody. The term "neutralizing antibody" as used herein refers to a monoclonal antibody which is capable of specifically binding to hVEGF or hVEGF-related protein, and which is capable of substantially inhibiting or eliminating the mitogenic activity of one or more of such proteins with which it reacts. Typically a neutralizing antibody will inhibit such mitogenic activity at least about 50%, and preferably greater than 80%, as determined, for example, by an in vitro cell survival or proliferation assay, such as described in Example 2. The neutralizing antibodies of the invention are especially useful in therapeutic applications, to prevent or treat unwanted endothelial cell proliferation or neovascularization.

After hybridoma cells are identified that produce antibodies of the desired specificity, affinity, and/or neutralization activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

For some therapeutic and diagnostic applications, it is desirable that the monoclonal antibody be reactive with fewer than all of the different proteins within the group of hVEGF and hVEGF-related proteins. For example, it may be desirable to have a monoclonal antibody that is capable of specifically binding to hVEGF but not to hVEGF-related proteins. Such antibodies are readily identified by comparative ELISA assays or comparative immunoprecipitation of hVEGF and each of the hVEGF-related proteins.

The monoclonal antibodies secreted by the subclones are suitably separated from the culture medium, ascites fluid, or serum by conventional immnunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese Hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., Proc. Nat. Acad. Sci. 81:6851 (1984), or by covalently joining to the immunoglobulin coding sequence all or part of the coding sequence for a non-immunoglobulin polypeptide. Such non-immunoglobulin polypeptides include polypeptide toxins such as ricin, diphtheria toxin, or Pseudomonas exotoxin (to produce immunotoxins), viral sequences, cellular receptors such as a T-cell receptor, cytokines such as TNF, interferons, or interleukins, and other biologically or immunologically active polypeptides. In that manner, "chimeric" or "hybrid" antibodies are prepared that have the binding specificity of an anti-hVEGF or anti-hVEGF-related protein monoclonal antibody.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for hVEGF or hVEGF-related protein and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be hVEGF, hVEGF-related protein, an immunologically reactive portion thereof) to compete with the test sample analyte (hVEGF or hVEGF-related protein) for binding with a limited amount of antibody. The amount of hVEGF or hVEGF-related protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the invention also are useful for in vivo imaging, wherein an antibody labeled with a detectable moiety is administered to a host, preferably into the bloodstream, and the presence and location of the labeled antibody in the host is assayed. This imaging technique is useful in the staging and treatment of neoplasms. The antibody may be labeled with any moiety that is detectable in a host, whether by nuclear magnetic resonance, radiology, or other detection means known in the art.

For therapeutic applications, the antibodies of the invention may be administered to a mammal, preferably a human, in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes. The antibody is also suitably administered by intratumoral, peritumoral, intralesional, or perilesional routes, to exert local as well as systemic therapeutic effects.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

For the prevention or treatment of disease, the appropriate dosage of antibody will depend on the type of disease to be treated, as defined above, the severity and course of the disease, whether the antibodies are administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 0.015 to 15 mg/kg of antibody is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

According to another embodiment of the invention, the effectiveness of the antibody in preventing or treating disease may be improved by administering the antibody serially or in combination with another agent that is effective for those purposes, such as another antibody directed against a different epitope or neutralizing a different protein than the first antibody, or one or more conventional therapeutic agents such as, for example, alkylating agents, folic acid antagonists, anti-metabolites of nucleic acid metabolism, antibiotics, pyrimidine analogs, 5-fluorouracil, purine nucleosides, anines, amino acids, triazol nucleosides, corticosteroids, calcium, retinoids, lipoxygenase and cyclooxygenase inhibitors, fumaric acid and its salts, analgesics, psychopharmaceuticals, local anesthetics, spasmolytics, and beta-blockers. Such other agents may be present in the composition being administered or may be administered separately. Also, the antibody is suitably administered serially or in combination with radiological treatments, whether involving irradiation or administration of radioactive substances.

The antibodies of the invention also are useful as affinity purification agents. In this process, the antibodies against hVEGF or hVEGF-related protein are immobilized on a suitable support, such a Sephadex resin or filter paper, using methods well known in the art. The immobilized antibody then is contacted with a sample containing the hVEGF or hVEGF-related protein to be purified, and thereafter the support is washed with a suitable solvent that will remove substantially all the material in the sample except the hVEGF or hVEGF-related protein, which is bound to the immobilized antibody. Finally, the support is washed with another suitable solvent, such as glycine buffer, pH 5.0, that will release the hVEGF or hVEGF-related protein from the antibody.

The following examples are offered by way of illustration only and are not intended to limit the invention in any manner. All patent and literature references cited herein are expressly incorporated.

EXAMPLE 1

Preparation of Monoclonal Antibodies

To obtain hVEGF conjugated to keyhole limpet hemocyanin (KLH) for immunization, recombinant hVEGF (165 amino acids), Leung, et al., Science 246:1306 (1989), was mixed with KLH at a 4:1 ratio in the presence of 0.05% glutaraldehyde and the mixture was incubated at room temperature for 3 hours with gentle stirring. The mixture then was dialyzed against phosphate buffered saline (PBS) at 4° C. overnight.

BALB/c mice were immunized four times every two weeks by intraperitoneal injections with 5 $\mu$g of hVEGF conjugated to 20 $\mu$g of KLH, and were boosted with the same dose of hVEGF conjugated to KLH four days prior to cell fusion.

Spleen cells from the immunized mice were fused with P3X63Ag8U.1 myeloma cells, Yelton, et al., Curr. Top. Microbiol. Immunol. 81:1 (1978), using 35% polyethylene glycol (PEG) as described. Yarmush, et al., Proc. Nat. Acad. Sci. 77:2899 (1980). Hybridomas were selected in HAT medium.

Supernatants from hybridoma cell cultures were screened for anti-hVEGF antibody production by an ELISA assay using hVEGF-coated microtliter plates. Antibody that was bound to hVEGF in each of the wells was determined using alkaline phosphatase-conjugated goat anti-mouse IgG immunoglobulin and the chromogenic substrate p-nitrophenyl phosphate. Harlow & Lane, *Antibodies: A Laboratory Manual*, p.597 (Cold Spring Harbor Laboratory, 1988). Hybridoma cells thus determined to produce anti-hVEGF antibodies were subcloned by limiting dilution, and two of those clones, designated A4.6.1 and B2.6.2, were chosen for further studies.

The A4.6.1 and B2.6.2 hybridoma cell lines have been deposited on Mar. 29, 1991 with the American Type Culture Collection (ATCC), 10801 University Boulevard, Manassas, Va. 20110-2209.

EXAMPLE 2

Characterization of Monoclonal Antibodies

A. Antiqen Specificity

The binding specificities of the anti-hVEGF monoclonal antibodies produced by the A4.6.1 and B2.6.2 hybridomas were determined by ELISA. The monoclonal antibodies were added to the wells of microtiter plates that previously had been coated with hVEGF, FGF, HGF, or epidermal growth factor (EGF). Bound antibody was detected with peroxidase conjugated goat antimouse IgG immunoglobulins. The results of those assays confirmed that the monoclonal antibodies produced by the A4.6.1 and B2.6.2 hybridomas bind to hVEGF, but not detectably to those other protein growth factors.

B. Epitope Mapping

A competitive binding ELISA was used to determine whether the monoclonal antibodies produced by the A4.6.1 and B2.6.2 hybridomas bind to the same or different epitopes (sites) within hVEGF. Kim, et al., Infect. Immun. 57:944 (1989). Individual unlabeled anti-hVEGF monoclonal antibodies (A4.6.1 or B2.6.2) or irrelevant anti-HGF antibody (IgG1 isotype) were added to the wells of microtiter plates that previously had been coated with hVEGF. Biotinylated anti-hVEGF monoclonal antibodies (BIO-A4.6.1 or BIO-B2.6.2) were then added. The ratio of biotinylated antibody to unlabeled antibody was 1:1000. Binding of the biotinylated antibodies was visualized by the addition of avidin-conjugated peroxidase, followed by o-phenylenediamine dihydrochloride and hydrogen peroxide. The color reaction, indicating the amount of biotinylated antibody bound, was determined by measuring the optical density (O.D) at 495 nm wavelength.

Figure 1B:
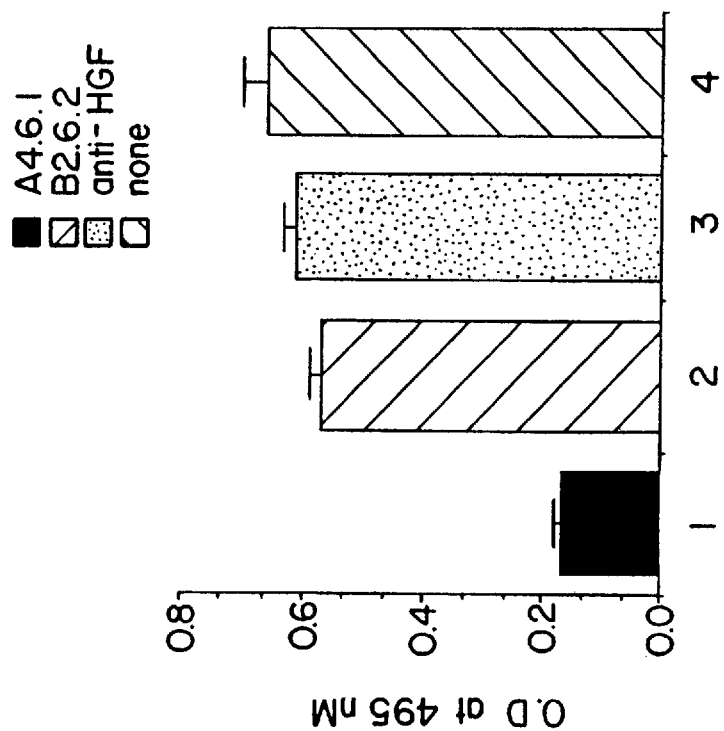

As shown in FIG. 1, in each case, the binding of the biotinylated anti-hVEGF antibody was inhibited by the corresponding unlabeled antibody, but not by the other unlabeled anti-hVEGF antibody or the anti-HGF antibody. These results indicate that the monoclonal antibodies produced by the A4.6.1 and B2.6.2 hybridomas bind to different epitopes within hVEGF.

C. Isotyping

The isotypes of the anti-hVEGF monoclonal antibodies produced by the A4.6.1 and B2.6.2 hybridomas were determined by ELISA. Samples of culture medium (supernatant) in which each of the hybridomas was growing were added to the wells of microtiter plates that had previously been coated with hVEGF. The captured anti-hVEGF monoclonal antibodies were incubated with different isotype-specific alkaline phosphatase-conjugated goat anti-mouse immunoglobulins, and the binding of the conjugated antibodies to the anti-hVEGF monoclonal antibodies was determined by the addition of p-nitrophenyl phosphate. The color reaction was measured at 405 nm with an ELISA plate reader.

By that method, the isotype of the monoclonal antibodies produced by both the A4.6.1 and B2.6.2 hybridomas was determined to be IgG1.

D. Binding Affinity

The affinities of the anti-hVEGF monoclonal antibodies produced by the A4.6.1 and B2.6.2 hybridomas for hVEGF were determined by a competitive binding assays. A predetermined sub-optimal concentration of monoclonal antibody was added to samples containing 20,000–40,000 cpm $^{125}$I-hVEGF (1–2 ng) and various known amounts of unlabeled hVEGF (1–1000 ng). After 1 hour at room temperature, 100 $\mu$l of goat anti-mouse Ig antisera (Pel-Freez, Rogers, AR USA) were added, and the mixtures were incubated another hour at room temperature. Complexes of antibody and bound protein (immune complexes) were precipitated by the addition of 500 μl of 6% polyethylene glycol (PEG, mol. wt. 8000) at 40° C., followed by centrifugation at 2000×G. for 20 min. at 4° C. The amount of $^{125}$I-hVEGF bound to the anti-hVEGF monoclonal antibody in each sample was determined by counting the pelleted material in a gamma counter.

Affinity constants were calculated from the data by Scatchard analysis. The affinity of the anti-hVEGF monoclonal antibody produced by the A4.6.1 hybridoma was calculated to be $1.2 \times 10^9$ liters/mole. The affinity of the anti-hVEGF monoclonal antibody produced by the B2.6.2 hybridoma was calculated to be $2.5 \times 10^9$ liters/mole.

E. Inhibition of hVEGF Mitogenic Activity

Bovine adrenal cortex capillary endothelial (ACE) cells, Ferrara, et al., Proc. Nat. Acad. Sci. 84:5773 (1987), were seeded at a density of $10^4$ cells/ml in 12 multiwell plates, and 2.5 ng/ml hVEGF was added to each well in the presence or absence of various concentrations of the anti-hVEGF monoclonal antibodies produced by the A4.6.1 or B2.6.2 hybridomas, or an irrelevant anti-HGF monoclonal antibody. After culturing 5 days, the cells in each well were counted in a Coulter counter. As a control, ACE cells were cultured in the absence of added hVEGF.

Figure 2:
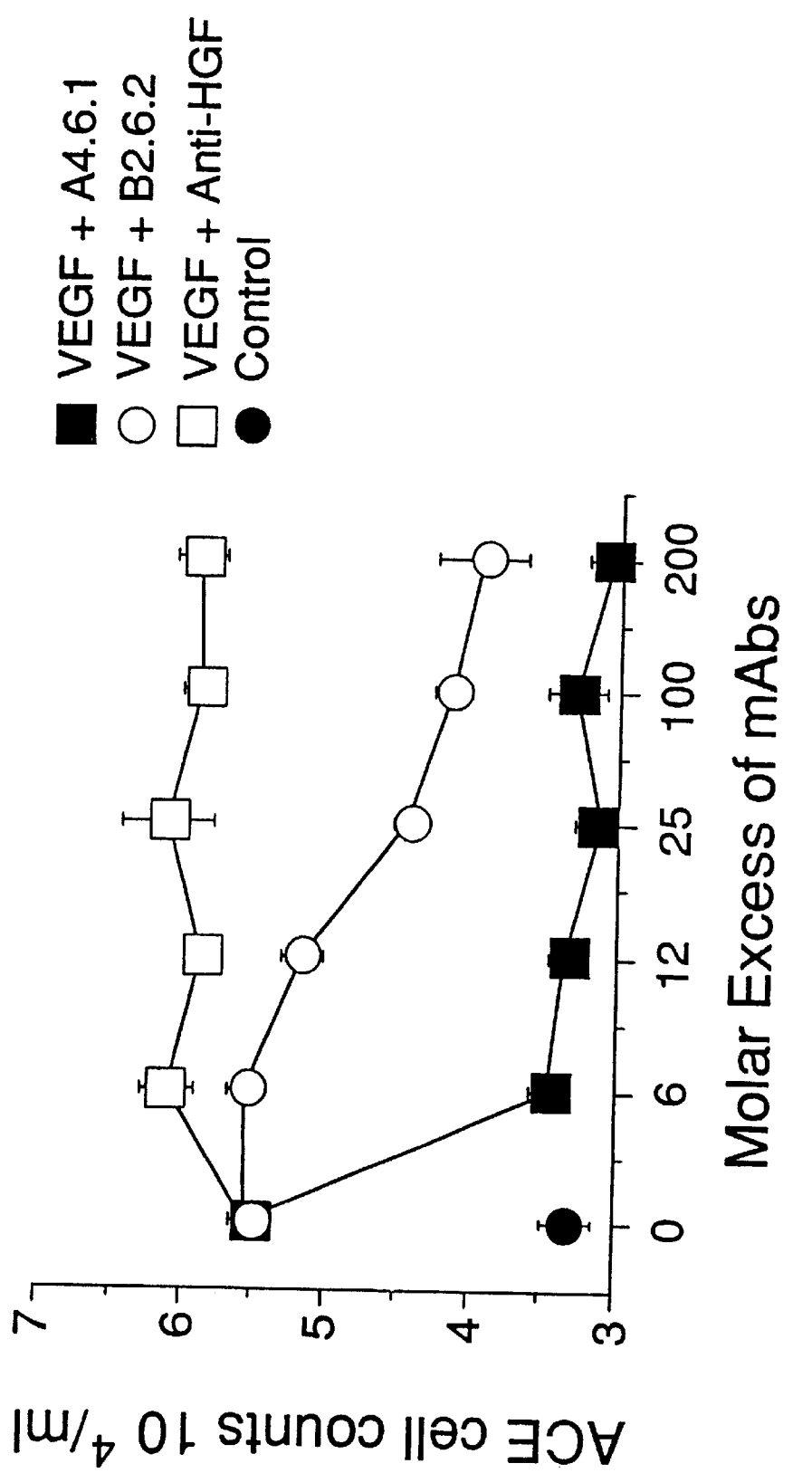
FIG. 2 shows the effect of anti-hVEGF monoclonal antibodies (A4.6.1 or B2.6.2) or an irrelevant anti-HGP antibody on the biological activity of hVEGF in cultures of bovine adrenal cortex capillary endothelial (ACE) cells.

As shown in FIG. 2, both of the anti-hVEGF monoclonal antibodies inhibited the ability of the added hVEGF to support the growth or survival of the bovine ACE cells. The monoclonal antibody produced by the A4.6.1 hybridoma completely inhibited the mitogenic activity of hVEGF, whereas the monoclonal antibody produced by the B2.6.2 hybridoma only partially inhibited the mitogenic activity of hVEGF.

F. Inhibition of hVEGF Binding

Bovine ACE cells were seeded at a density of $2.5 \times 10^4$ cells/0.5 ml/well in 24 well microtiter plates in Dulbecco's Modified Eagle's Medium (DMEM) containing 10% calf serum, 2 mM glutamine, and 1 ng/ml basic fibroblast growth factor. After culturing overnight, the cells were washed once in binding buffer (equal volumes of DMEM and F12 medium plus 25 mM HEPES and 1% bovine serum albumin) at 4° C.

12,000 cpm $^{125}$I-hVEGF (approx. $5 \times 10^4$ cpm/ng/ml) was preincubated for 30 minutes with 5 μg of the anti-hVEGF monoclonal antibody produced by the A4.6.1, B2.6.2, or A2.6.1 hybridoma (250 μl total volume), and thereafter the mixtures were added to the bovine ACE cells in the microtiter plates. After incubating the cells for 3 hours at 4° C., the cells were washed 3 times with binding buffer at 4° C., solubilized by the addition of 0.5 ml 0.2 N. NaOH, and counted in a gamma counter.

Figure 3A:
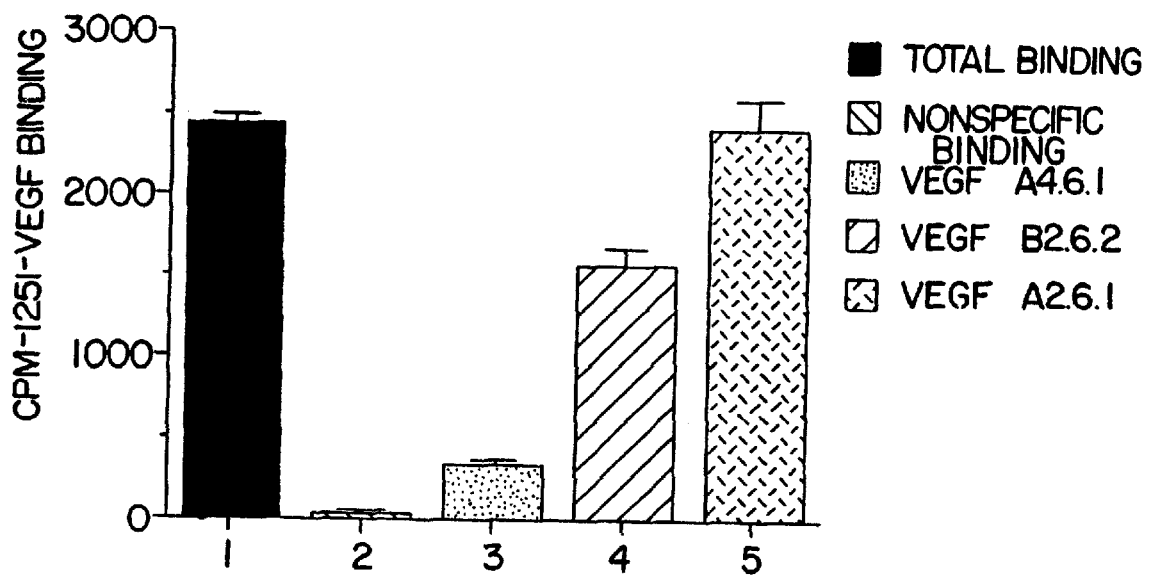
FIG. 3 shows the effect of anti-hVEGF monoclonal antibodies (A4.6.1, B2.6.2, or A2.6.1) on the binding of hVEGF to bovine ACE cells.
Figure 3B:
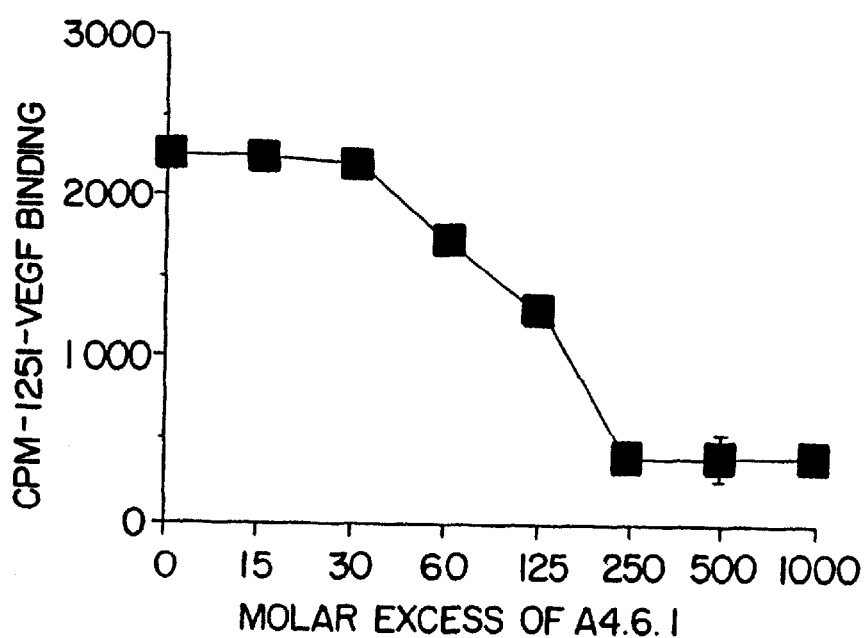

As shown in FIG. 3 (upper), the anti-hVEGF monoclonal antibodies produced by the A4.6.1 and B2.6.2 hybridomas inhibited the binding of hVEGF to the bovine ACE cells. In contrast, the anti-hVEGF monoclonal antibody produced by the A2.6.1 hybridoma had no apparent effect on the binding of hVEGF to the bovine ACE cells. Consistent with the results obtained in the cell proliferation assay described above, the monoclonal antibody produced by the A4.6.1 hybridoma inhibited the binding of hVEGF to a greater extent than the monoclonal antibody produced by the B2.6.2 hybridoma.

As shown in FIG. 3 (lower), the monoclonal antibody produced by the A4.6.1 hybridoma completely inhibited the binding of hVEGF to the bovine ACE cells at a 1:250 molar ratio of hVEGF to antibody.

G. Cross-reactivity with VEGF-related Proteins

To determine whether the anti-hVEGF monoclonal antibody produced by the A4.6.1 hybridoma is reactive with hVEGF-related protein, the antibody was assayed for its ability to immunoprecipate hVEGF-related protein.

Human 293 cells were transfected with vectors comprising the nucleotide coding sequence of the 121- and 189-amino acid hVEGF-related proteins, as described. Leung, et al., Science 246:1306 (1989). Two days after transfection, the cells were transferred to medium lacking cysteine and methionine. The cells were incubated 30 minutes in that medium, then 100 μCi/ml of each $^{35}$S-methionine and $^{35}$S-cysteine were added to the medium and the cells were incubated another two hours. The labeling was chased by transferring the cells to serum free medium and incubating three hours. The cell culture media were collected, and the cells were lysed by incubating for 30 minutes in lysis buffer (150 mM NaCl, 1% NP40, 0.5% deoxycholate, 0.1% sodium dodecyl sulfate (SDS), 50 mM Tris, pH 8.0). Cell debris was removed from the lysates by centrifugation at 200×G. for 30 minutes.

500 μsamples of cell culture media and cell lysates were incubated with 2 μl of A4.6.1 hybridoma antibody (2.4 mg/ml) for 1 hour at 4° C., and then were incubated with 5 μl of rabbit anti-mouse IgG immunoglobulin for 1 hour at 4° C. Immune complexes of $^{35}$S-labeled hVEGF-related protein and anti-hVEGF monoclonal antibody were precipitated with protein-A sepharose (Pharmacia), then subjected to SDS—12% polyacrylamide gel electrophoresis under reducing conditions. The gel was exposed to x-ray film for analysis of the immunoprecipitated, radiolabeled proteins by autoradiography.

The results of that analysis indicated that the anti-hVEGF monoclonal antibody produced by the A4.6.1 hybridoma was cross-reactive with both the 121- and 189-amino acid hVEGF-related proteins.

What is claimed is:

1. The hybridoma cell deposited under American Type Culture Collection Accession Number ATCC HB10709 (referred to herein as A4.6.1).

2. The hybridoma cell deposited under American Type Culture Collection Accession Number ATCC HB10710 (referred to herein as B2.6.2).

3. A monoclonal antibody produced by the hybridoma cell of claim 1.

4. A monoclonal antibody produced by the hybridoma cell of claim 2.

* * * * *